(12) United States Patent
Schuetz

(10) Patent No.: US 11,370,738 B2
(45) Date of Patent: Jun. 28, 2022

(54) PROCESS FOR THE PRODUCTION OF 2-METHYL-4-(2,6,6-TRIMETHYL-1-CYCLOHEXEN-1-YL)-2-BUTENAL

(71) Applicant: DSM IP ASSETS B.V., Heerlen (NL)

(72) Inventor: Jan Schuetz, Kaiseraugst (CH)

(73) Assignee: DSM IP ASSETS B.V., Heerlen (NL)

( * ) Notice: Subject to any disclaimer, the term of this patent is extended or adjusted under 35 U.S.C. 154(b) by 0 days.

(21) Appl. No.: 17/046,483

(22) PCT Filed: Apr. 8, 2019

(86) PCT No.: PCT/EP2019/058787
§ 371 (c)(1),
(2) Date: Oct. 9, 2020

(87) PCT Pub. No.: WO2019/197326
PCT Pub. Date: Oct. 17, 2019

(65) Prior Publication Data
US 2021/0130277 A1    May 6, 2021

(30) Foreign Application Priority Data

Apr. 11, 2018  (EP) ..................................... 18166706

(51) Int. Cl.
*C07C 45/58*      (2006.01)
*C07C 47/225*     (2006.01)

(52) U.S. Cl.
CPC ............ *C07C 45/58* (2013.01); *C07C 47/225* (2013.01); *C07C 2601/16* (2017.05)

(58) Field of Classification Search
CPC ............................ C07C 45/58; C07C 2601/16
See application file for complete search history.

(56) References Cited

U.S. PATENT DOCUMENTS 2,369,156 A    2/1945  Milas
2,451,740 A    10/1948 Lindlar

FOREIGN PATENT DOCUMENTS

| CH | 255097   | 6/1948 |
| EP | 1 764 359 | 3/2007 |
| GB | 1156818  | 7/1969 |

OTHER PUBLICATIONS

International Search Report for PCT/EP2019/058787, dated Jun. 13, 2019, 4 pages.
Written Opinion of the ISA for PCT/EP2019/058787, dated Jun. 13, 2019, 6 pages.

*Primary Examiner* — Sikarl A Witherspoon
(74) *Attorney, Agent, or Firm* — Nixon & Vanderhye P.C.

(57) ABSTRACT

The present invention relates to an improved way to produce 2-methyl-4-(2,6,6-trimethyl-1-cyclohexen-1-yl)-2-butenal and derivatives thereof.

10 Claims, No Drawings

PROCESS FOR THE PRODUCTION OF 2-METHYL-4-(2,6,6-TRIMETHYL-1-CYCLOHEXEN-1-YL)-2-BUTENAL

This application is the U.S. national phase of International Application No. PCT/EP2019/058787 filed 8 Apr. 2019, which designated the U.S. and claims priority to EP Patent Application No. 18166706.4 filed 11 Apr. 2018, the entire contents of each of which are hereby incorporated by reference.

The present invention relates to an improved way to produce 2-methyl-4-(2,6,6-trimethyl-1-cyclohexen-1-yl)-2-butenal and derivatives thereof.

2-Methyl-4-(2,6,6-trimethyl-1-cyclohexen-1-yl)-2-butenal, which is the compound of formula (I) when $R_1$ is H

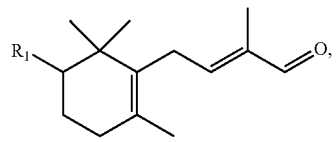
(I)

is an important intermediate for example in the production of Vitamin A.

Due to the importance of 2-methyl-4-(2,6,6-trimethyl-1-cyclohexen-1-yl)-2-butenal and its derivatives the objective of the present invention was to provide an improved process for the production of the compound of formula (I). Because of the improvement of the process, the selectivity of the process was increased significantly and furthermore less by-product (waste) formation was obtained.

The synthesis of the compound of 2-methyl-4-(2,6,6-trimethyl-1-cyclohexen-1-yl)-2-butenal and its derivatives is carried out according to the following reaction scheme:

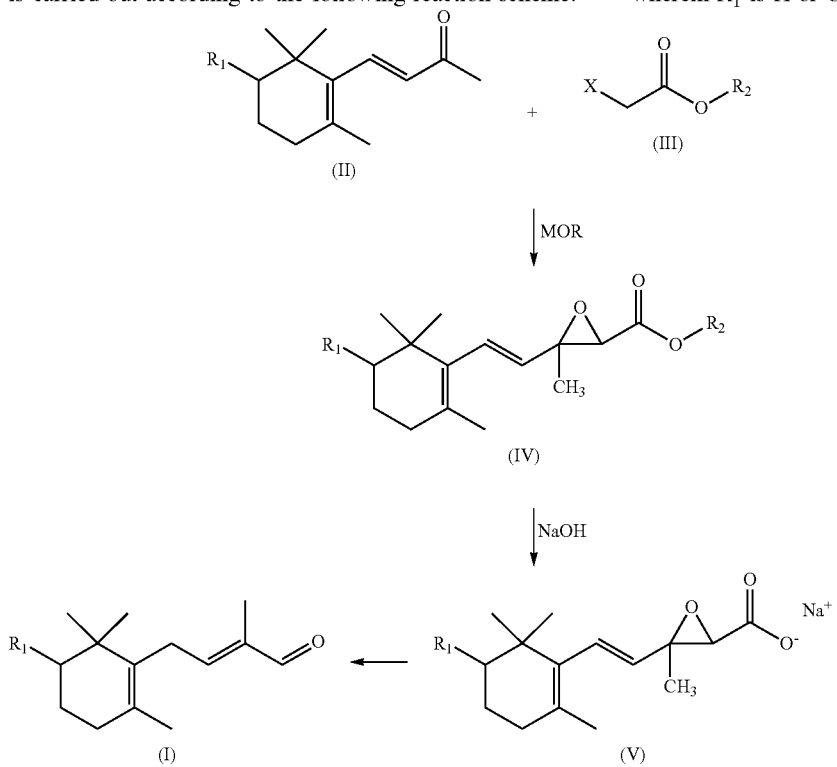

whereby all substituents are defined below.

Therefore, the present invention relates to a process (P) to produce the compound of formula (I)

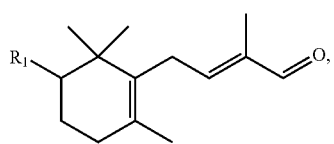
(I)

wherein as first step (step (i))

a Darzens reaction is carried out between a compound of formula (II)

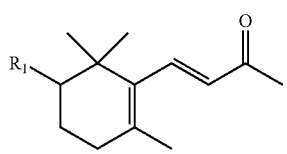
(II)

wherein $R_1$ is H or $CH_3$, preferably wherein $R_1$ is H, and a compound of formula (III)

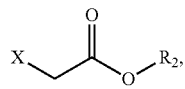

wherein X is Cl or Br, preferably wherein X is Cl, and R₂ is C₁-C₄-alkyl, preferably R₂ is methyl or ethyl, in the presence of MOR,
wherein R is a C₁-C₄-alkyl group (preferably methyl or ethyl), and
M signifies Na⁺, K⁺ or Cs⁺,
wherein between 1.0 and 1.3 mol equivalents of the compound of formula (III) (based on the amount of the compound of formula (II)) and between 1.0 and 1.4 mol equivalent of MOR (based on the amount of the compound of formula (II)) is used, followed by a second step (ii) whereby a saponification reaction in the presence of NaOH to form the compound of formula (V)

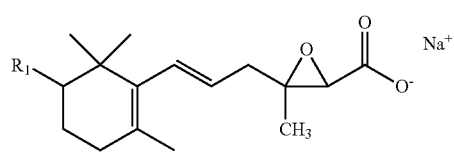

takes place, and
the compound of formula (V) is undergoing a decarboxylation reaction to form the compound of formula (I), wherein a reaction temperature of less than 30° C. is applied.

In the following the 2 steps are discussed in more detail.

Step (i)

The first reaction step (step (i)) is in fact a sequence of two steps, step (ia) and step (ib), which are performed without isolating the reaction product of the first reaction step, i.e. the compound of formula (IV).

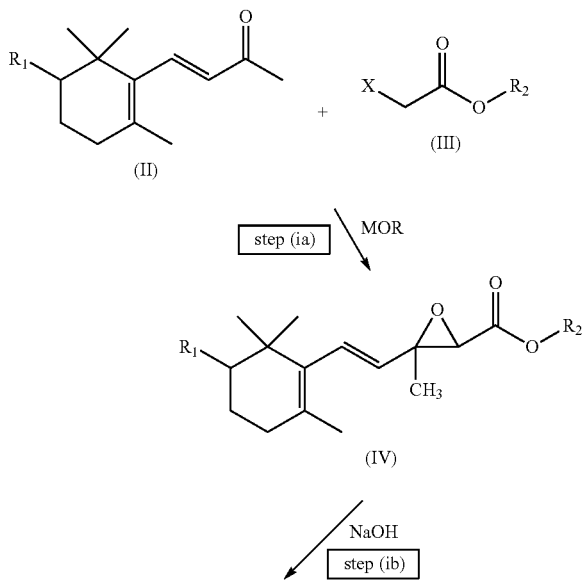

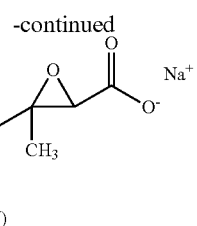

Step (ia) is a glycidic ester condensation, whereby an α,β-epoxy ester (=glycidic ester) is saponified to the corresponding carboxylate (step (ib)).

It was found that it is very advantageous to use MOR (in liquid or in solid form), wherein R is a C₁-C₄-alkyl group (preferably methyl or ethyl, more preferably methyl) and M signifies Na⁺, K⁺ or Cs⁺, as a base and methyl chloroacetate or methyl bromoacetate (preferably methyl chloroacetate) as α-haloester at a temperature in the range of from −5° to 30° C.

Step (ia) is usually carried out at lower temperatures than step (ib). Step (ia) is usually carried out at a temperature in the range of from −5° C. to 5° C. and step (ib) at a temperature in the range of from 15 to 30° C., preferably at room temperature (25° C.).

An essential feature of the first step is that from 1.0 mol equivalents up to 1.3 mol equivalents of the compound of formula (III), based on the amount of the compound of formula (II), and from 1.0 mol equivalents up to 1.4 mol equivalents of MOR, based on the amount of the compound of formula (II), are used.

It is also possible to isolate the reaction product of step (ia), if needed and desired.

Step (i), i.e. step (ia) and step (ib), is usually carried out in a solvent or a mixture of solvents.

Suitable solvents are aliphatic alcohols, aliphatic hydrocarbons, or aromatic hydrocarbons, as well as mixtures thereof. Especially suitable are aliphatic C₁-C₆ alcohols (such as methanol, ethanol, iso-propanol), and aliphatic C₅-C₁₀-hydrocarbons such as n-heptane, n-hexane, and cyclohexane, as well as mixtures thereof. Suitable aromatic hydrocarbons are i.e. toluene, o-xylene, m-xylene and p-xylene.

Therefore, the present invention relates to a process (P1), which is process (P), wherein step (i) is carried out in at least one solvent.

Therefore, the present invention relates to a process (P1'), which is process (P1), wherein step (i) is carried out in at least one aliphatic alcohol, at least one aliphatic hydrocarbon and/or at least one aromatic hydrocarbon.

Therefore, the present invention relates to a process (P1"), which is process (P1), wherein step (i) is carried out in at least one solvent chosen from aliphatic C₁-C₆ alcohols (such as methanol, ethanol, iso-propanol, EtOH, iPrOH), n-heptane, n hexane, and cyclohexane.

The reaction temperature of step (ia) is preferably in the range of from −5° C. to 5° C.

Therefore, the present invention relates to a process (P2), which is process (P), (P1), (P1') or (P1'''), wherein step (ia) is carried out at a reaction temperature of in the range of from −5° C. to 5° C.

An essential feature of the first step is that from 1.0 mol equivalents up to 1.3 mol equivalents of the compound of formula (III), based on the amount of the compound of formula (II), and from 1.0 mol equivalents up to 1.4 mol equivalents of MOR, based on the amount of the compound of formula (II), are used.

Preferably from 1.0 mol equivalents t up to 1.2 mol equivalents of the compound of formula (III), based on the amount of the compound of formula (II), and from 1.0 mol equivalents up to 1.3 mol equivalents of MOR, based on the amount of the compound of formula (II), are used.

More preferably from 1.0 mol equivalents up to 1.1 mol equivalents of the compound of formula (III), based on the amount of the compound of formula (II), and from 1.0 mol equivalents up to 1.2 mol equivalents of MOR [especially preferred from 1.0 mol equivalents to up to 1.1 mol equivalents of MOR, based on the amount of the compound of formula (II)] are used.

Therefore, the present invention relates to a process (P3), which is process (P), (P1), (P1'), (P1''') or (P2), wherein from 1.0 mol equivalents up to 1.2 mol equivalents of the compound of formula (III), based on the amount of the compound of formula (II), and from 1.0 mol equivalents up to 1.3 mol equivalents of MOR, based on the amount of the compound of formula (II), are used.

Therefore, the present invention relates to a process (P3'), which is process (P), (P1), (P1'), (P1'') or (P2), wherein from 1.0 mol equivalents up to 1.1 mol equivalents of the compound of formula (III), based on the amount of the compound of formula (II), and from 1.0 mol equivalents up to 1.2 mol equivalents of MOR, especially preferred from 1.0 mol equivalents up to 1.2 mol equivalents, based on the amount of the compound of formula (II), are used.

Step (ib) is carried out a reaction temperature of less than 30° C. Preferably step (ib) is carried out a reaction temperature in the range of from 15° C. to 30° C., more preferably at a temperature in the range of from 15° C. to 30° C., most preferably at room temperature (25° C.).

Therefore, the present invention relates to a process (P4), which is process (P), (P1), (P1'), (P1'''), (P2), (P2'), (P2''), (P3) or (P3'), wherein step (ib) is carried out a temperature in the range of from 15° C. to 30° C.

Therefore, the present invention relates to a process (P4'), which is process (P), (P1), (P1'), (P1''), (P2), (P2'), (P2''), (P3) or (P3'), wherein step (ib) is carried out at room temperature.

The reaction product of step (i), which is the compound of formula (V), is extracted from the reaction mixture by an aromatic or aliphatic hydrocarbon, such as preferably benzene, toluene, n-heptane, n hexane or cyclohexane. It can be washed with an aqueous phase.

Usually the reaction product is not isolated completely but left solved in the solvent of the reaction mixture.

Step (ii)

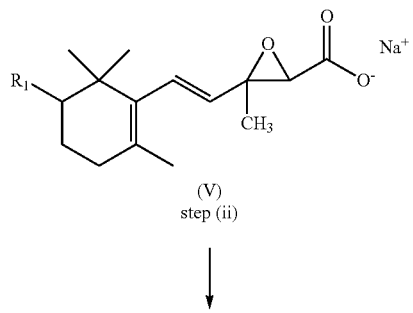

(V)
step (ii)

↓

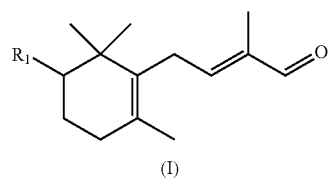

(I)

The reaction product of step (i), which is the compound of formula (V) in at least one aliphatic hydrocarbon or aromatic hydrocarbon, especially in n-heptane, n-hexane, and/or cyclohexane, is decarboxylated without heating the solution at all. Step (ii) can be carried out at low temperatures (in the range of from 15 to 30° C.) or even at room temperature as well as under normal pressure.

Therefore, the present invention relates to a process (P5), which is process (P), (P1), (P1'), (P1'''), (P2), (P2'), (P2''), (P3), (P3'), (P4) or (P4'), wherein step (ii) is carried out at a temperature in the range of from 15 to 30° C.

Therefore, the present invention relates to a process (P5'), which is process (P), (P1), (P1'), (P1''), (P2), (P2'), (P2''), (P3), (P3'), (P4) or (P4'), wherein step (ii) is carried out at room temperature.

Therefore, the present invention relates to a process (P6), which is process (P), (P1), (P1'), (P1''), (P2), (P2'), (P2''), (P3), (P3'), (P4), (P4'), (P5) or (P5'), wherein step (ii) is carried out under normal pressure.

This is surprising since such a step is usually carried out at elevated temperatures and usually also under reduced pressure.

The final product (compound of formula (I)), is preferably isolated by distillation.

The selectivity of the process according to the present invention is improved significantly despite using very mild reaction conditions.

The invention is illustrated by the following Example. All percentages are related to the weight and the temperature is given in ° C. min=minute(s)

EXAMPLES

Example 1

β-Ionone (17.6 ml, 84 mmol), chloroacetic acid methyl ester (8.2 ml, 93 mmol), methanol (1.9 ml) and n-hexane (1.9 ml) were added to a flask. The solution was cooled to 0° C. Sodium methylate (5.00 g, 93 mmol) was slowly added. The reaction mixture was warmed to room temperature and stirred for 30 min. Aqueous sodium hydroxide (10 ml) in methanol (90 ml) was added over 30 min. Water (150 ml) was added. The reaction mixture was stirred for 10 min. n-Hexane (40 ml) was added and the layers were separated. The aqueous layer was extracted with n-hexane (2×50 ml). The combined organic layers were washed twice with acetic acid (2×16 ml). The organic layer was dried over Na₂SO₄, filtered, and concentrated in vacuo. 2-Methyl-4-(2,6,6-trimethyl-1-cyclohexen-1-yl)-2-butenal was obtained (21.0 g, 82% yield, quantitative conversion).

The invention claimed is:

1. A process for the production of a compound of formula (I):

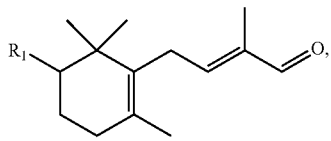

the process comprising the steps of:
(i) forming a compound of formula (V):

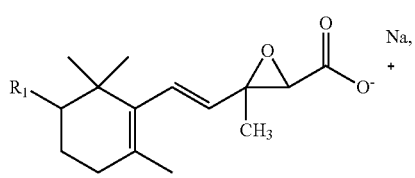

wherein
R₁ is H or CH₃, by the steps comprising:
(ia) forming a Darzens reaction product between
(1) a compound of formula (II):

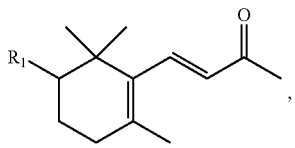

wherein
R₁ is as defined previously, and
(2) a compound of formula (III):

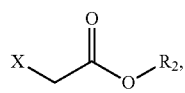

wherein
X is Cl or Br, preferably wherein X is Cl, and
R₂ is $C_1$-$C_4$-alkyl, wherein
by carrying out the Darzens reaction between the compounds of formulas (II) and (III) at a reaction temperature in a range from −5° C. to 5° C. in the presence of MOR, wherein R is a $C_1$-$C_4$-alkyl group and M signifies Na⁺, K⁺ or Cs⁺, and with from 1.0 to 1.1 mol equivalents of the compound of formula (III), based on the amount of the compound of formula (II), and from 1.0 to 1.1 mol equivalents of MOR, based on the amount of the compound of formula (II), and thereafter
(ib) conducting a saponification reaction of the Darzens reaction product of step (ia) at room temperature (25° C.) in the presence of NaOH to form the compound of formula (V), and then subsequently without heating,
(ii) subjecting the compound of formula (V) to a decarboxylation reaction at room temperature (25° C.) to obtain the compound of formula (I).

2. The process according to claim 1, wherein step (i) is carried out in at least one solvent.

3. The process according to claim 2, wherein step (i) is carried out in at least one aliphatic alcohol, in at least one aliphatic hydrocarbon, and/or in at least one aromatic hydrocarbon.

4. The process according to claim 3, wherein step (i) is carried out in at least one solvent selected from the group consisting of aliphatic $C_1$-$C_6$ alcohols and aliphatic $C_5$-$C_{10}$-hydrocarbons.

5. The process according to claim 1, wherein step (ii) is carried out under normal pressure.

6. The process according to claim 1, wherein R is methyl or ethyl.

7. The process according to claim 1, wherein the Darzens reaction product is a compound of formula (IV):

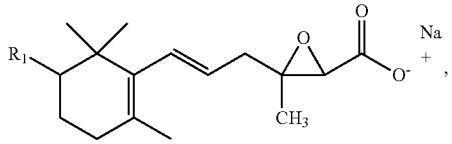

wherein
R1 and R2 are as defined previously.

8. The process according to claim 7, wherein the step (ia) is practiced without isolating the compound of formula (IV).

9. The process according to claim 8, wherein step (ii) is practiced without heating the compound of formula (V).

10. The process according to claim 1, wherein the compound of formula (III) is chloroacetic acid methyl ester and MOR is sodium methylate.

* * * * *